United States Patent [19]

Griffith

[11] Patent Number: 5,290,251
[45] Date of Patent: Mar. 1, 1994

[54] METHOD OF CYSTOSTOMY TUBE IMPLANTATION

[75] Inventor: Donald P. Griffith, Houston, Tex.

[73] Assignee: URO Research, Inc., Houston, Tex.

[21] Appl. No.: 80,559

[22] Filed: Jun. 21, 1993

Related U.S. Application Data

[62] Division of Ser. No. 615,896, Nov. 20, 1990, Pat. No. 5,234,408.

[51] Int. Cl.⁵ ............................................. A61M 3/32
[52] U.S. Cl. ................................ 604/175; 623/12; 128/898; 600/30
[58] Field of Search ............... 604/93, 174, 175, 178, 604/264–266, 280; 623/1, 11, 12; 600/29, 30; 128/898

[56] References Cited

U.S. PATENT DOCUMENTS

| | | |
|---|---|---|
| 3,540,451 | 11/1970 | Zeman . |
| 3,717,151 | 2/1973 | Collett . |
| 4,217,664 | 8/1980 | Faso ................................ 623/12 |
| 4,338,937 | 7/1982 | Lerman ........................... 623/12 |
| 4,338,937 | 7/1982 | Lerman . |
| 4,534,761 | 8/1985 | Raible ............................. 604/175 |
| 4,623,348 | 11/1986 | Feit . |
| 4,642,104 | 2/1987 | Sakamoto et al. . |
| 4,863,438 | 9/1989 | Gauderer et al. . |
| 4,934,999 | 6/1990 | Bader . |
| 4,959,054 | 9/1990 | Heimke et al. . |
| 4,969,202 | 11/1990 | Ravo ................................ 623/12 |
| 4,976,735 | 12/1990 | Griffith et al. ................. 623/12 |
| 5,013,717 | 5/1991 | Solomon et al. . |
| 5,019,393 | 5/1991 | Ito et al. . |
| 5,035,711 | 7/1991 | Aoki et al. . |
| 5,085,646 | 2/1992 | Svensson et al. .............. 623/12 |
| 5,234,408 | 8/1993 | Griffith ............................ 604/93 |

FOREIGN PATENT DOCUMENTS 0194980 2/1986 European Pat. Off. .
8601729 3/1986 World Int. Prop. O. .

OTHER PUBLICATIONS

Campbell's Urology, published by W. B. Saunders Company 5th Edition, pp. 2116–2119; (1986).

Atlas of Urological Surgery, published by W. B. Saunders Company, 1989, authored by Frank Hinman, Jr., pp. 505–507.

Urological Surgery, 2d Edition, published by Harper & Row, edited by James Glenn and William Boyce, pp. 304–305.

Catalog from Bard Urological Division, C. R. Bard, Inc., Covington, Georgia 30209.

Publication by Cook Urological, Inc., 1100 West Morgan Street, P.O. Box 227, Spencer, Indiana 47460. (1987).

Primary Examiner—C. Fred Rosenbaum
Assistant Examiner—Cholin Smith
Attorney, Agent, or Firm—Rosenblatt & Associates

[57] ABSTRACT

The present invention relates to a tissue bondable cystostomy tube for use in a human patient. The present invention also relates to a method for surgically implanting the tissue bondable cystostomy tube in a human patient.

11 Claims, 3 Drawing Sheets

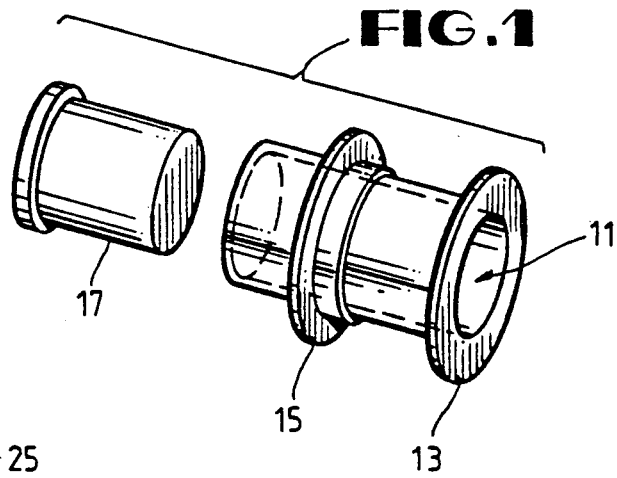
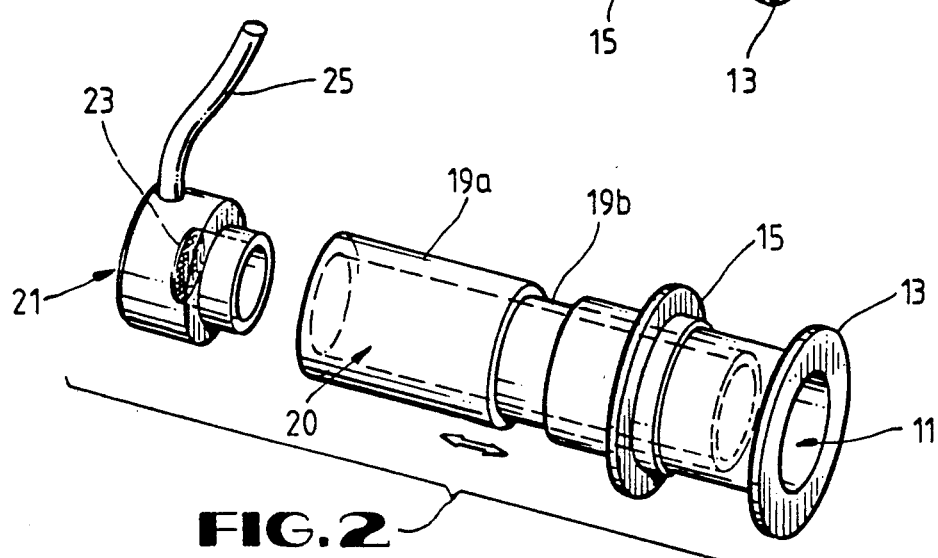
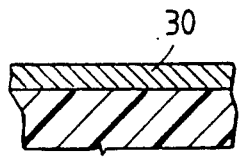
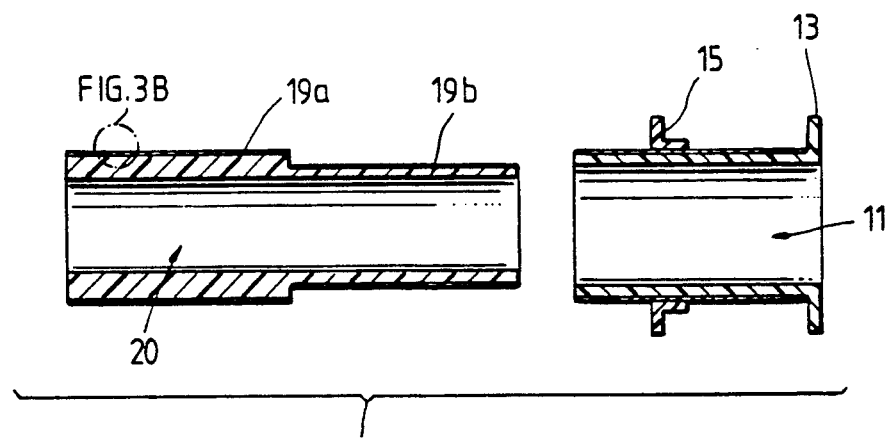

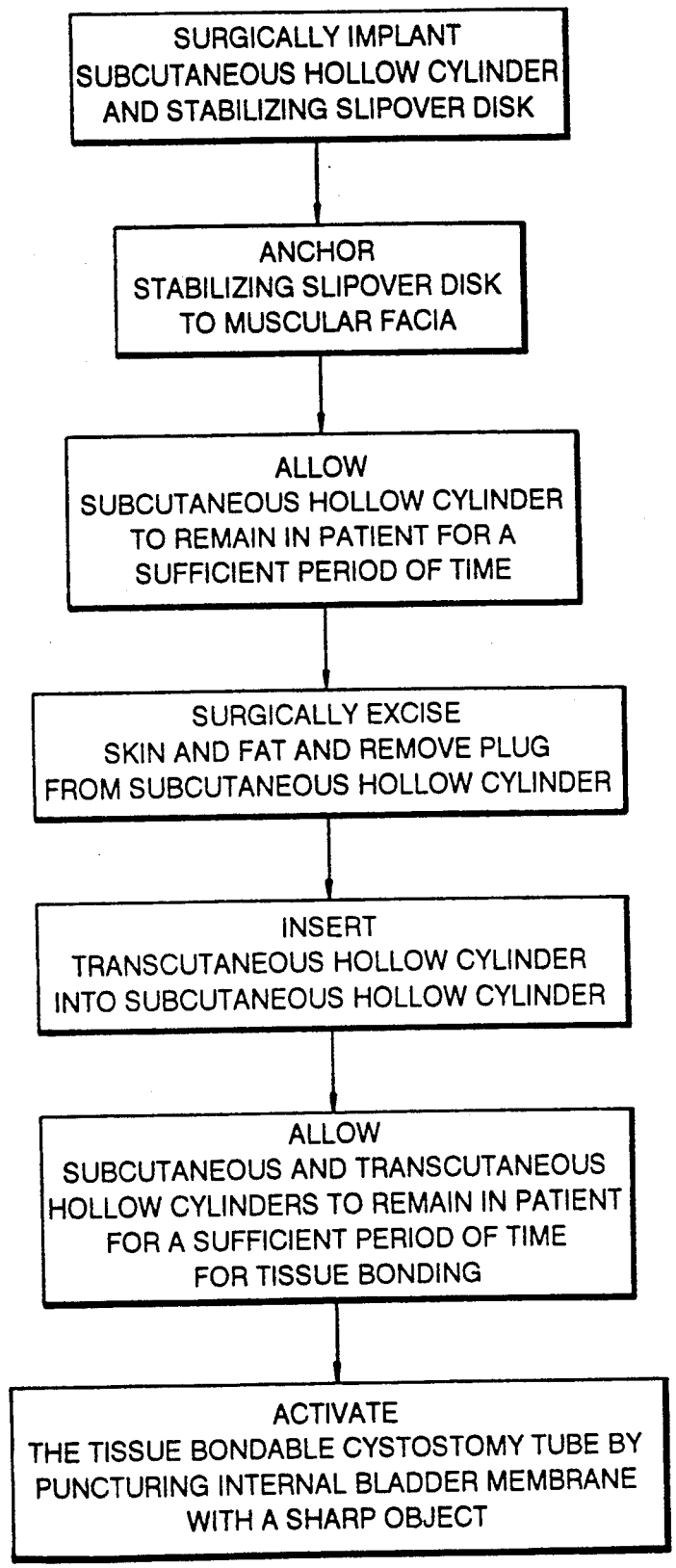

METHOD OF CYSTOSTOMY TUBE IMPLANTATION

This is a divisional application of application Ser. No. 07/615,896 filed on Nov. 20, 1990 now U.S. Pat. No. 5,234,408.

BACKGROUND OF THE INVENTION

1. Field of the Invention

The present invention relates to a tissue bondable cystostomy tube for use in a human patient. The invention, more particularly, concerns a tissue bondable cystostomy tube comprising (1) a subcutaneous hollow cylinder, (2) a stabilizing slipover disc sleeve, (3) a transcutaneous hollow cylinder, and (4) an end cap.

The present invention also relates to the surgical procedure for implantation of the tissue bondable cystostomy tube. This procedure entails implantation of the device in a patient, bonding of the patient's tissue to the device, and activation of the device.

2. Description of the Prior Art

Cystostomy tubes have been known for many years. Cystostomy refers to the formation of an opening into the bladder. Cystostomy tubes are inserted into the opening in the bladder resulting from the cystostomy in order to provide a flow path for fluid contained in the bladder to a point external to the patient's body.

One of the oldest forms of cystostomy is suprapubic cystostomy. Suprapubic cystostomy is described in Cambell's Urology, 5th edition, W. B. Saunders Co. (1986), at page 2117.

There are many problems associated with suprapubic cystostomy. In some cases the bladder contracts down on the cystostomy tube and causes a ureterovesical obstruction. Another problem with suprapubic cystostomy results from the leakage of urine around the cystostomy tube and onto abdominal skin. Similarly, skin bacteria gain access to the urinary bladder resulting in urinary infection.

Another form of cystostomy is percutaneous cystostomy. Percutaneous cystostomy is described in Cambell's Urology. 5th edition, W. B. Saunders Co. (1986), at page 2117. Percutaneous cystostomy is sometimes referred to as "punch cystostomy." Percutaneous cystostomy also results in urinary leakage around the cystostomy tube onto the abdominal skin, and skin bacteria gain access to the urinary bladder. Percutaneous cystostomy thus also results in urinary infection.

SUMMARY OF THE INVENTION

The present invention provides a tissue bondable cystostomy tube which overcomes the problems of the prior art cystostomy tubes. The cystostomy tube of the present invention comprises a subcutaneous hollow cylinder having an upper end, a lower end, and a planar disc-like base, and a transcutaneous hollow cylinder having an upper end and a lower end. Both the subcutaneous hollow cylinder, including the planar disc-like base, and the transcutaneous hollow cylinder are coated on their exterior surfaces with a material suitable for bonding with biological tissue.

The planar disc-like base extends radially outward from the lower end of the subcutaneous hollow cylinder and provides a means for positioning and aligning the subcutaneous hollow cylinder with the bladder membrane.

A stabilizing slipover disc sleeve, coated on its exterior surface with a material suitable for bonding with biological tissue, is centrally located on the exterior surface of the subcutaneous hollow cylinder. The slipover disc sleeve provides a means for properly aligning and stabilizing the cystostomy tube in the patient. The slipover disc sleeve may be altered during surgical implantation so as to be customized to an individual patient.

The lower end of the transcutaneous hollow cylinder is slidably received into the upper end of the subcutaneous hollow cylinder. When implanted in the patient, the upper end of the transcutaneous hollow cylinder extends outside the patient's body forming an abdominal stoma. A removable cap can be affixed to the upper end of the transcutaneous hollow cylinder.

The present invention also relates to a surgical procedure for implanting the tissue bondable cystostomy tube. This procedure takes place in multiple phases which facilitate the bacterial resistant bonding of the tissue to the cystostomy tube. This tissue bonding entails biological bonding between the cystostomy tube and (1) the bladder detrusor muscle, (2) the skin, and (3) the muscle and fascia of the abdominal wall. This tissue bonding resists urinary leakage and prevents skin bacteria from easily gaining access to the urinary bladder. As long as the abdominal stoma portion of the cystostomy tube remains capped, bacterial access to the bladder should not occur. Thus, the urinary infection problems associated with prior art cystostomy tubes are overcome by the present invention.

The first step in the method for implanting the tissue bondable cystostomy tube is to surgically implant the subcutaneous hollow cylinder in the region of the bladder membrane. During this implantation phase, the subcutaneous hollow cylinder contains a plug. Concurrent with implantation, the stabilizing slipover disc sleeve is also custom trimmed to properly align and stabilize the subcutaneous hollow cylinder. The skin is closed completely in this initial surgical procedure thereby burying the device in the abdominal wall and bladder muscle. This burying minimizes risk of bacterial contamination while tissue ingrowth into the device occurs.

The subcutaneous hollow cylinder is allowed to remain in the patient for a sufficient period of time for tissue bonding to occur. It is envisioned that several weeks and possibly several months will constitute a sufficient period of time for this tissue bonding to occur.

After this tissue bonding has occurred, a circular portion of skin and subcutaneous fat located above the subcutaneous hollow cylinder is surgically excised. The plug is then removed from the subcutaneous hollow cylinder.

Next, the lower end of the transcutaneous hollow cylinder is slidably inserted into the subcutaneous hollow cylinder. The inactivated subcutaneous and transcutaneous hollow cylinders are allowed to remain in the patient for a sufficient period of time for subcutaneous tissue and skin bonding to occur to the transcutaneous hollow cylinder.

The cystostomy tube is then activated by inserting a sharp object into the transcutaneous hollow cylinder and puncturing the internal bladder membrane. A cap is then affixed onto the upper end of the transcutaneous hollow cylinder.

BRIEF DESCRIPTION OF THE DRAWINGS

FIG. 1 is an exploded isometric view of the subcutaneous hollow cylinder, planar disc, stabilizing slipover disc sleeve, and plug.

FIG. 2 is an exploded isometric diagram of the planar disc, subcutaneous hollow cylinder, stabilizing slipover disc sleeve, transcutaneous hollow cylinder, and cap.

FIG. 3a is a side cross-sectional view of the transcutaneous hollow cylinder, subcutaneous hollow cylinder, stabilizing slipover disc sleeve, and planar disc.

FIG. 3b is an enlarged view of the cylinder wall and tissue bonding coating. Proplast ® and Dacron ® are examples of tissue bonding coatings.

FIG. 8 is a block diagram of the surgical implantation procedure.

DESCRIPTION OF THE PREFERRED EMBODIMENT

Figure 4:
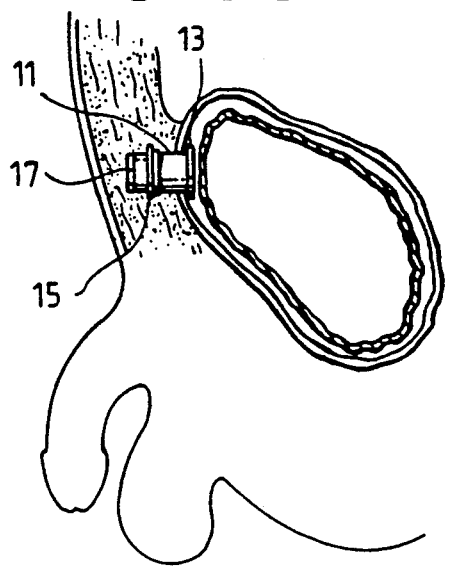
FIG. 4 is a side view of the planar disc, subcutaneous hollow cylinder, and stabilizing slipover disc sleeve implanted in the patient after the first step in the surgical implantation procedure.

The subcutaneous hollow cylinder 11 having an upper end and a lower end is shown in FIG. 1. A planar disc-like base 13 extends radially outward from the lower end of the subcutaneous hollow cylinder 11. In a preferred embodiment, the planar disc-like base 13 is integrally formed with the subcutaneous hollow cylinder 11. A stabilizing slipover disc sleeve 15 is centrally located on the exterior surface of the subcutaneous hollow cylinder 11. During the initial stage of the method for implanting the tissue bondable cystostomy tube, a plug 17 is contained with the subcutaneous hollow cylinder 11. In a preferred embodiment, the plug 17 is a Teflon ® plug 17.

Referring to FIG. 2, a transcutaneous hollow cylinder 20, having an upper end 19a and a lower end 19b, is slidably received in the upper end of the subcutaneous hollow cylinder 11. A removable cap 21 is affixed to the upper end of the transcutaneous hollow cylinder 20. As shown in FIG. 2, the removable cap 21 comprises an antimicrobial filter 23 internally mounted in the cap 21 and a drainage tube 25 attached to the cap 21. In a preferred embodiment, the drainage tube 25 is sufficiently long to extend into a leg bag attached to the patient's leg. The antimicrobial filter 23 serves as a bacterial filter 23 which prevents infected urine in the leg bag from reflexing back into the urinary bladder.

Referring to FIG. 3a, the lower end 19b of the transcutaneous hollow cylinder 20 has an outer diameter sized to fit snugly within the subcutaneous hollow cylinder 11. The upper end 19a of the transcutaneous hollow cylinder 20 has an outer diameter equal to the outer diameter of the subcutaneous hollow cylinder 11.

Referring to FIGS. 3a and 3b, the transcutaneous hollow cylinder 20, subcutaneous hollow cylinder 11, stabilizing slipover disc sleeve 15, and planar disc-like base 13 are all coated on their exterior surface with a material suitable for bonding with biological tissue 30. In a preferred embodiment, the material suitable for bonding with biological tissue is Proplast ®.

The present invention also extends to a method for implanting the tissue bondable cystostomy tube. As shown in FIGS. 4 and 8, the first step in the implantation process involves surgically implanting a subcutaneous hollow cylinder 11 coated on its exterior surface with a material suitable for bonding with biological tissue 30 in the region of the bladder membrane. In a preferred embodiment, the stabilizing slipover disc sleeve 15 is centrally located on the exterior surface of the subcutaneous hollow cylinder 11 at the time the subcutaneous hollow cylinder 11 is surgically implanted.

The next step in the implantation process involves anchoring the stabilizing slipover disc sleeve 15 to muscular fascia in the patient using sutures to ensure proper alignment of the transcutaneous hollow cylinder 20 and subcutaneous hollow cylinder 11, as shown in FIG. 8. The stabilizing slipover disc sleeve 15 is also coated on its exterior surface with a material suitable for bonding with biological tissue. During this implantation process, the subcutaneous hollow cylinder 11 contains a plug 17. In a preferred embodiment, this plug 17 is a Teflon ® plug 17.

The subcutaneous hollow cylinder 11 is then allowed to remain in the patient for a sufficient period of time for tissue bonding to occur. In a preferred embodiment, the sufficient period of time for tissue bonding to occur is several weeks.

Figure 5:
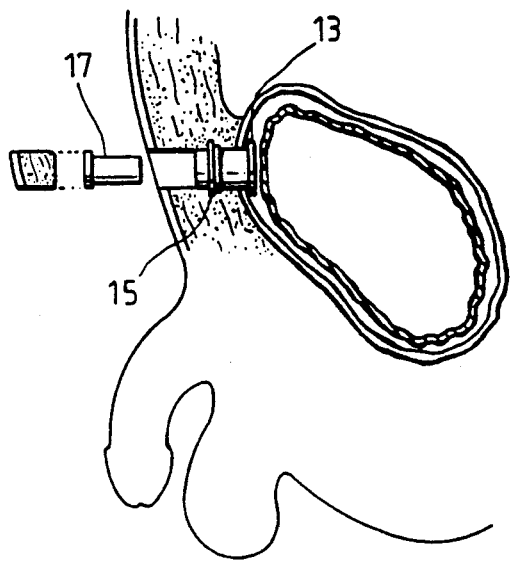
FIG. 5 is a side view of the surgical excision of the circular portion of skin and subcutaneous fat located above the subcutaneous hollow cylinder and the removal of the Teflon ® plug from the subcutaneous hollow cylinder during the surgical implantation procedure.

The next step in the surgical implantation process involves surgically excising a circular portion of skin and subcutaneous fat located above the subcutaneous hollow cylinder 11 and removing the plug 17 from the subcutaneous hollow cylinder 11, as shown in FIGS. 5 and 8.

Figure 6:
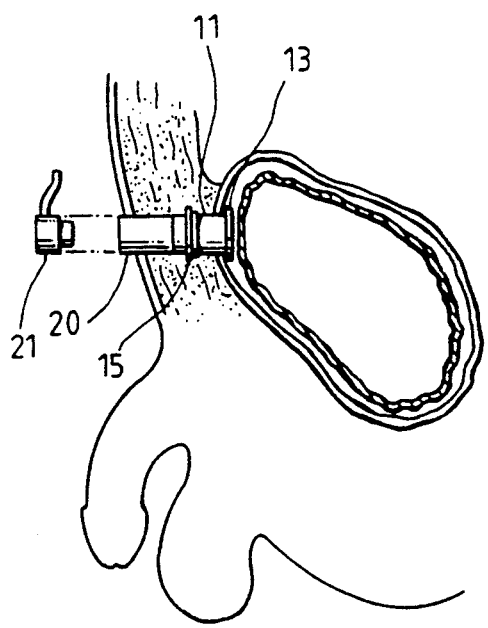
FIG. 6 is a side view of the tissue bondable cystostomy tube implanted in the patient.

Referring to FIGS. 6 and 8, the next step in the implantation process involves surgically implanting the transcutaneous hollow cylinder 20 by passing the transcutaneous hollow cylinder 20 through the opening created by the excision of skin and subcutaneous fat and slidably inserting the lower end 19b of the transcutaneous hollow cylinder 20 into the subcutaneous hollow cylinder 11. The subcutaneous hollow cylinder 11 and transcutaneous hollow cylinder 20 are then allowed to remain in the patient for a sufficient period of time for tissue bonding to occur.

After implantation of the tissue bondable cystostomy tube, the device can then be activated. The tissue bondable cystostomy tube is activated by inserting a sharp object into the transcutaneous hollow cylinder 20 and puncturing the internal bladder membrane. In a preferred embodiment, the sharp object inserted into the transcutaneous hollow cylinder 20 to puncture the internal bladder membrane is a trocar.

Figure 7:
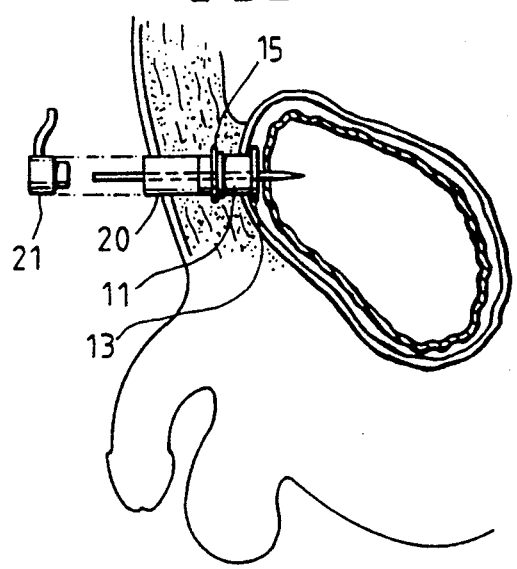
FIG. 7 is a side view of the activation of the tissue bondable cystostomy tube in the patient using a sharp object to puncture the internal bladder membrane.

As shown in FIGS. 6 and 7, the transcutaneous hollow cylinder 20 is inserted such that a portion of the upper end 19a of the transcutaneous hollow cylinder 20 extends outside the patient's body. As shown in FIG. 6, a cap 21 can be affixed to the upper end of the transcutaneous hollow cylinder 20. So long as this cap 21 remains fixed, bacterial access to the bladder should not occur. The present invention allows the placement of antimicrobial agents directly through the abdominal stoma into the urinary bladder to treat and prevent chronic urinary infection.

Many modifications and variations may be made in the embodiments described herein and depicted in the accompanying drawings without departing from the concept of the present invention. Accordingly, it is clearly understood that the embodiments described and illustrated herein are illustrative only and are not intended as a limitation upon the scope of the present invention.

What is claimed is:

1. A method for implanting a tissue bondable cystostomy tube in a patient comprising:
   a. surgically implanting a subcutaneous hollow cylinder coated on its exterior surface with a material suitable for bonding with biological tissue in the region of the bladder membrane, said subcutaneous hollow cylinder containing a plug;
   b. allowing the subcutaneous hollow cylinder to remain in the patient for a sufficient period of time for tissue bonding to occur;
   c. surgically excising a circular portion of skin and subcutaneous fat located above said subcutaneous hollow cylinder and removing the plug from said subcutaneous hollow cylinder;
   d. surgically implanting a transcutaneous hollow cylinder having an upper end and a lower end and coated on its exterior surface with a material suitable for bonding with biological tissue by passing the transcutaneous hollow cylinder through the opening created by the excision of skin and subcutaneous fat and slidably inserting the lower end of the transcutaneous hollow cylinder into the subcutaneous hollow cylinder; and
   e. allowing the subcutaneous and transcutaneous hollow cylinders to remain in the patient for a sufficient period of time for tissue bonding to occur.

2. The method of claim 1 wherein the plug contained in the subcutaneous hollow cylinder is a Teflon plug.

3. The method of claim 1 wherein the sufficient period of time for tissue bonding to occur is several weeks.

4. The method of claim 1 further comprising the step of activating the tissue bondable cystostomy tube by inserting a sharp object into the transcutaneous hollow cylinder and puncturing the internal bladder membrane.

5. The method of claim 4 wherein the sharp object inserted into the transcutaneous hollow cylinder to puncture the internal bladder membrane is a trocar.

6. The method of claim 1 wherein a portion of the upper end of the transcutaneous hollow cylinder extends outside the patient after surgical implantation of the transcutaneous hollow cylinder.

7. The method of claim 6 further comprising the step of affixing a cap on the upper end of the transcutaneous hollow cylinder.

8. A method for implanting a tissue bondable cystostomy tube in a patient comprising:
   a. surgically implanting a subcutaneous hollow cylinder having a stabilizing slipover disc sleeve centrally located on its exterior surface in the region of the bladder membrane, said subcutaneous hollow cylinder containing a plug and both said subcutaneous hollow cylinder and said stabilizing slipover disc sleeve coated on their exterior surfaces with a material suitable for bonding with biological tissue;
   b. anchoring the stabilizing slipover disc sleeve to muscular fascia in the patient using sutures to ensure proper alignment of the transcutaneous hollow cylinder and subcutaneous hollow cylinder;
   c. allowing the subcutaneous hollow cylinder to remain in the patient for a sufficient period of time for tissue bonding to occur;
   d. surgically excising a circular portion of skin and subcutaneous fat located above said subcutaneous hollow cylinder and removing the plug from said subcutaneous hollow cylinder;
   e. passing a transcutaneous hollow cylinder having an upper end and a lower end through the opening created by the excision of skin and subcutaneous fat and inserting the lower end of the transcutaneous hollow cylinder into the subcutaneous hollow cylinder; and
   f. allowing the subcutaneous and transcutaneous hollow cylinders to remain in the patient for a sufficient period of time for tissue bonding to occur.

9. The method of claim 8 further comprising the step of activating the tissue bondable cystostomy tube by inserting a sharp object into the transcutaneous hollow cylinder and puncturing the internal bladder membrane.

10. The method of claim 8 wherein the transcutaneous hollow cylinder is inserted such that the upper end of it extends outside the patient's body.

11. The method of claim 10 further comprising the step of affixing a cap on the upper end of the transcutaneous hollow cylinder.

* * * * *